Figure 8:
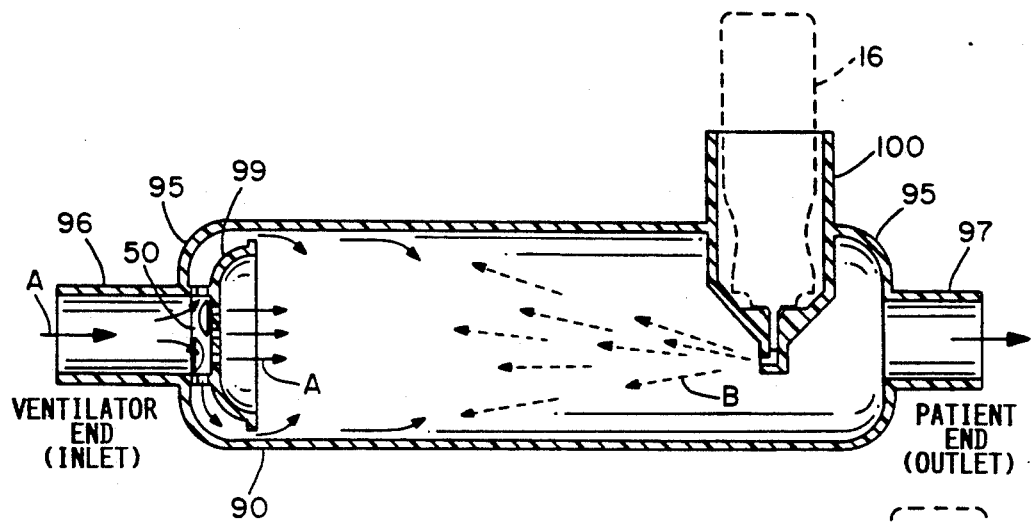
Figure 9:
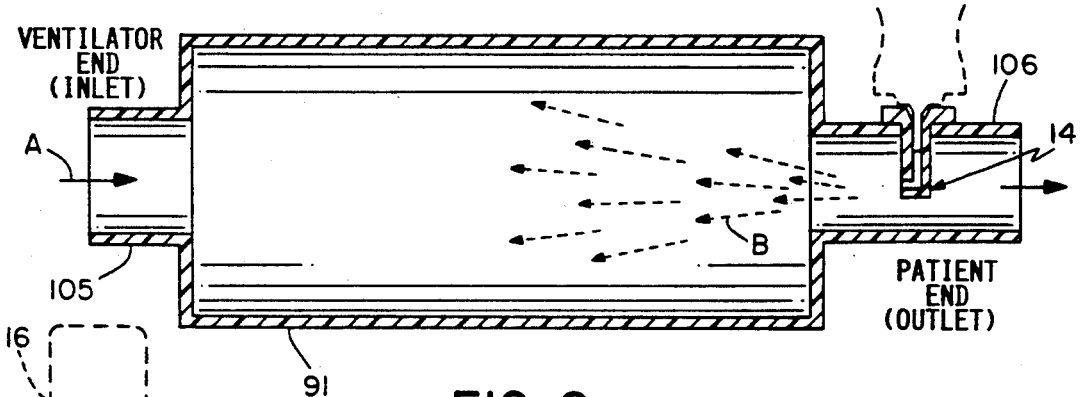
Figure 10:
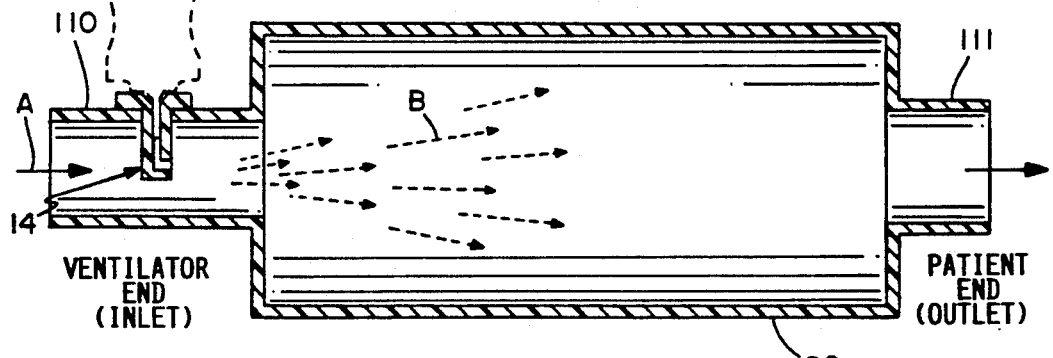

United States Patent [19]

Walstrom et al.

[11] Patent Number: 5,178,138
[45] Date of Patent: Jan. 12, 1993

[54] DRUG DELIVERY DEVICE

[76] Inventors: Dennis R. Walstrom, 251 W. Lake St., Excelsior, Minn. 55331; Steven R. Maslonka, 16163 Overlook Dr., Shakopee, Minn. 55379; Wade J. Scoles, East 20504 S. Altamont Blvd., Spokane, Wash. 99202

[21] Appl. No.: 580,804
[22] Filed: Sep. 11, 1990
[51] Int. Cl.$^5$ ............................................. A61M 11/00
[52] U.S. Cl. ........................... 128/200.23; 128/200.14; 128/203.12; 128/203.23
[58] Field of Search ....................... 128/203.12, 203.25, 128/205.11, 203.23, 203.15, 203.21, 203.24, 200.21, 200.23, 200.14; 222/3, 635

[56] References Cited

U.S. PATENT DOCUMENTS

| | | | |
|---|---|---|---|
| 146,730 | 1/1874 | Vickers | 128/206.21 |
| 1,418,182 | 5/1922 | Tabor | 128/203.29 |
| 2,123,353 | 7/1938 | Catt | 128/204.13 |
| 2,631,757 | 3/1953 | Alexander | 222/82 |
| 2,670,739 | 3/1954 | McNeill | 128/200.18 |
| 2,788,784 | 4/1957 | Birch et al. | 128/200.23 |
| 2,872,923 | 2/1959 | Birch et al. | 128/200.23 |
| 2,890,697 | 6/1959 | VanSickle | 128/200.23 |
| 3,012,555 | 12/1961 | Meshberg | 128/200.23 |
| 3,302,374 | 2/1967 | Szekely | 128/200.18 |
| 3,356,088 | 12/1967 | Nelson | 128/200.23 |
| 3,490,452 | 1/1970 | Greenfield | 128/200.23 |
| 3,522,806 | 8/1970 | Szekely | 128/200.18 |
| 3,838,686 | 10/1974 | Szekely | 128/200.18 |
| 4,030,492 | 6/1977 | Simbruner | 128/200.21 |
| 4,470,412 | 9/1984 | Nowacki et al. | 128/200.18 |

(List continued on next page.)

FOREIGN PATENT DOCUMENTS

| | | | |
|---|---|---|---|
| 586002 | 10/1959 | Canada | 128/200.23 |
| 64512 | 5/1978 | Finland | |
| 1488249 | 10/1977 | United Kingdom | |
| 8802267 | 4/1988 | World Int. Prop. O. | 128/200.23 |
| 8803419 | 5/1988 | World Int. Prop. O. | 128/200.23 |

OTHER PUBLICATIONS

Crogan S. J., Bixhop, M. J., Delivery Efficiency of Metered Dose Aerosols Given via Endotracheal Tubes, Anesthesiology 1989; 70:1008–1010.
Minisymposium: Delivery of Aerosoloized Medications Respiratory Care, Oct. 1988, vol. 33, No. 10.
European Patent Application No. 0 275 105, filed Jan. 14, 1988; Inventor: Walker; Title: Airway Adapter.
"Portable Equipment for General Anaesthesia, General Analgesia, and Resuscitation"; *The Lancet;* Dec. 9, 1961, p. 1290.
Monaghan, 3 pg. brochure on AeroVent Holding Chamber (undated).
"A Comparison of Aerosol Deposition in the Lung (List continued on next page.)

*Primary Examiner*—Edgar S. Burr
*Assistant Examiner*—Eric P. Raciti
*Attorney, Agent, or Firm*—Palmatier, Sjoquist & Helget

[57] ABSTRACT

A spacer for delivering a maximum amount of a therapeutic agent to the lungs. The spacer may be connected in the inspiratory line running from a mechanical ventilator or hand held and operated manually by the nonintubated, spontaneously breathing patient or the intubated, spontaneously breathing patient. The spacer includes the following features to maximize dispersion of the agent into the fluid flow: a structure for spraying the therapeutic agent in a retrograde fashion to prevent loss of the therapeutic agent to the expiratory limb of the respiratory circuit; a frustoconical shape that reflects the cone-like pattern of an aerosol spray to minimize impaction of the sprayed agent on the inner surfaces of the spacer; and a baffle to readily mix the fluid with the therapeutic agent and deflect fluid flow along the inner walls of the spacer where the therapeutic agent may otherwise collect.

17 Claims, 3 Drawing Sheets

U.S. PATENT DOCUMENTS

| | | | |
|---|---|---|---|
| 4,484,577 | 11/1984 | Sackner et al. | 128/200.23 |
| 4,592,348 | 6/1986 | Waters, IV et al. | 128/200.23 |
| 4,598,704 | 7/1986 | Bordoni et al. | 128/200.18 |
| 4,796,614 | 1/1989 | Nowacki | 128/200.14 |
| 4,805,609 | 2/1989 | Roberts et al. | 128/200.21 |
| 4,823,784 | 4/1989 | Bordoni et al. | 128/200.14 |
| 4,852,561 | 8/1989 | Sperry | 128/200.23 |
| 4,926,852 | 5/1990 | Zoltan et al. | 128/200.23 |
| 4,938,210 | 7/1990 | Shene | 128/203.12 |
| 4,940,051 | 7/1990 | Lankinen | 128/200.18 |
| 4,972,830 | 11/1990 | Wong | 128/200.21 |
| 5,025,806 | 6/1991 | Palmer | 128/203.12 |
| 5,078,131 | 1/1992 | Foley | 128/203.15 |

OTHER PUBLICATIONS from Aerochamber vs. Nebulizer in Patients Receiving Mechanical Ventilation", H. D. Fuller et al. (Am. Rev. Resp. Dis. vol. 137; p. 60, 1988).

"Metered Dose Inhaler Actuator-Adapters: A Comparison of Particle Size and Drug Delivery Through an Endotracheal Tube", Richard P. Larson et al. (Resp. Care Nov. 1989, vol. 34, No. 11, p. 1029).

"Terbutaline Aerosol Given Through Pear Spacer in Acute Severe Asthma", M. D. L. Morgan et al., (British Medical Journal, vol. 285, pp. 849-850, Sep. 25, 1982).

"Deposition of Pressurized Suspension Aerosols Inhaled Through Extension Devices", S. P. Newman et al. (Am. Rev. Resp. Dis. 1981; 124:317-320).

One-page brochure DHD Medical Products showing the DHD NIF-TEE Non-Rebreathing T-Piece and its Family of Accessories (undated).

Marquest Respiratory Catelog, pp. 11-16, and 25-29 Front and Back Covers, and Index, showing Nebulizers and Metered Dose Inhaler Adapter Model #172275 (Copyright 1987).

Instrumentation Industries Inc. Catelog, p. 24, Table of Contents, and Front and Back Covers; 1989-1990 Edition.

Monaghan Medical Corp. Packet, 76 pages, showing the Aerochamber with Mask, the Aerochamber, and Publications Relating to the Aerochamber.

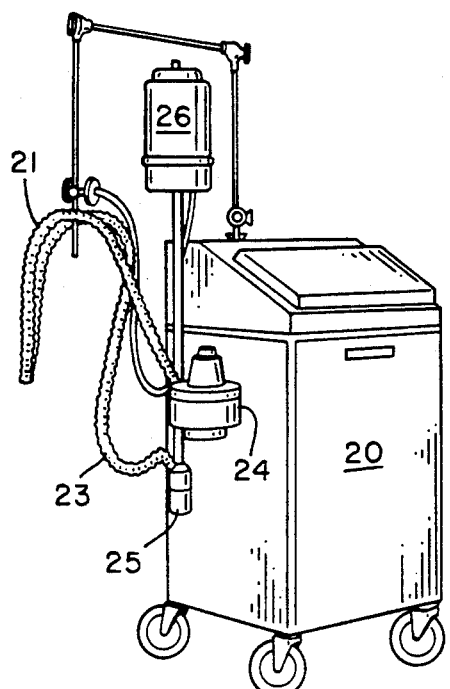
FIG. 1
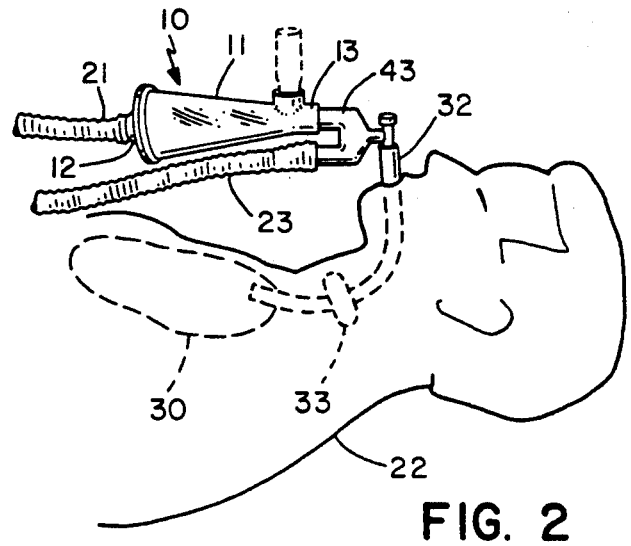
FIG. 2
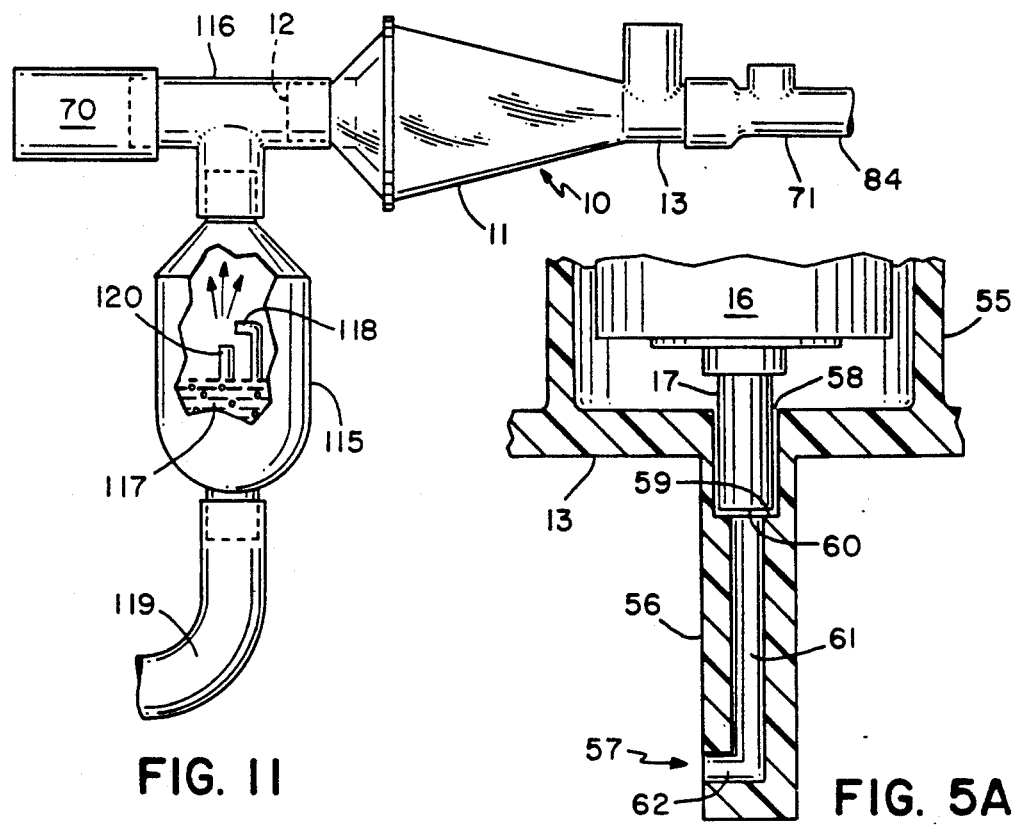
FIG. 11
FIG. 5A

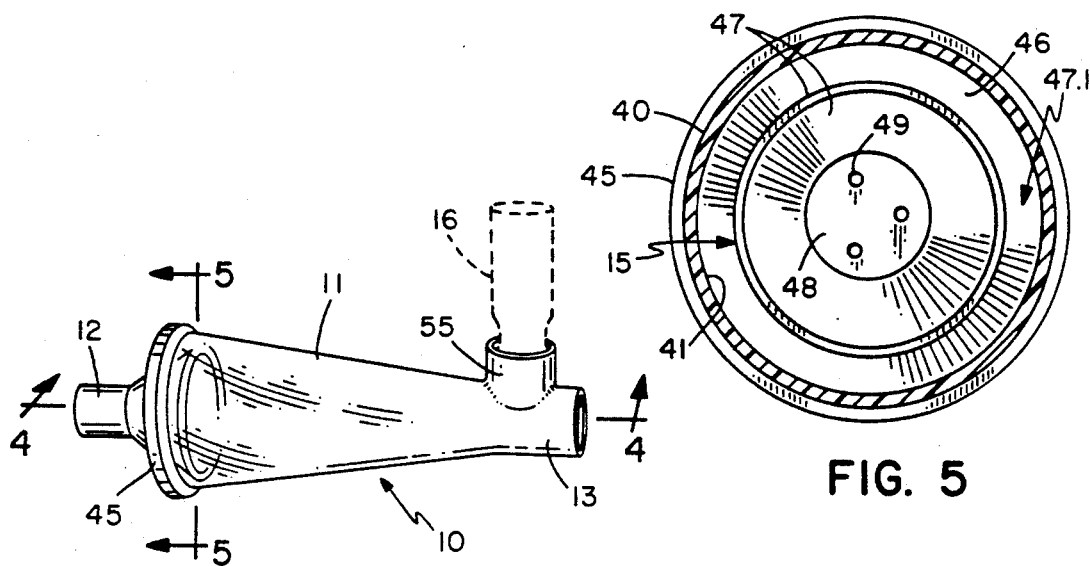
FIG. 3
FIG. 5
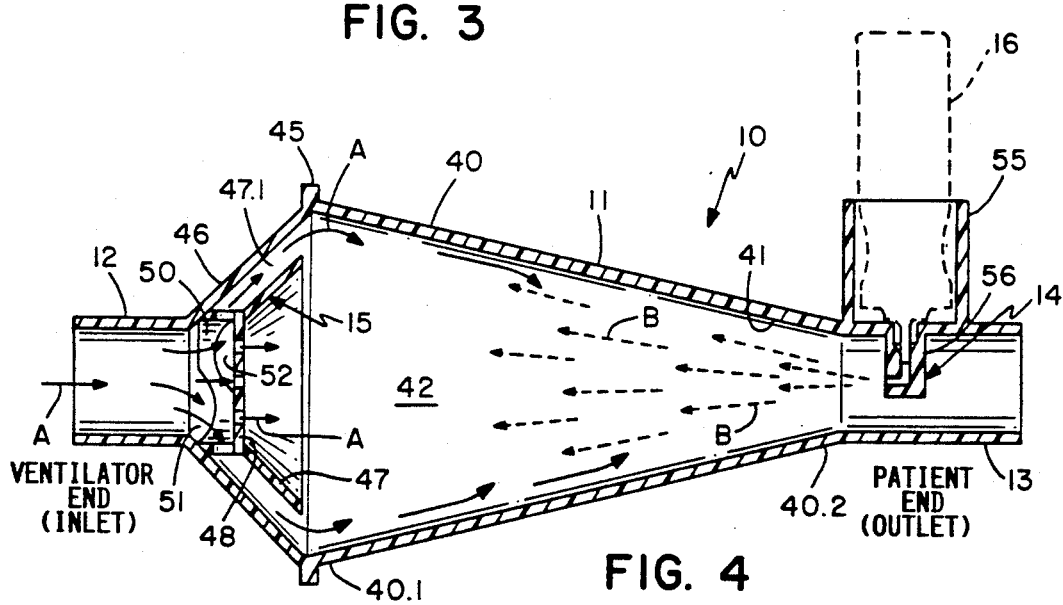
FIG. 4
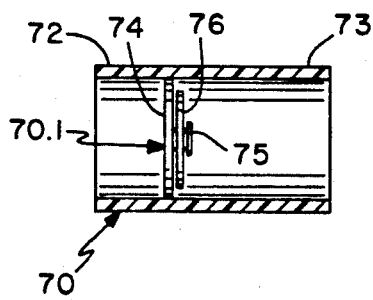
FIG. 6
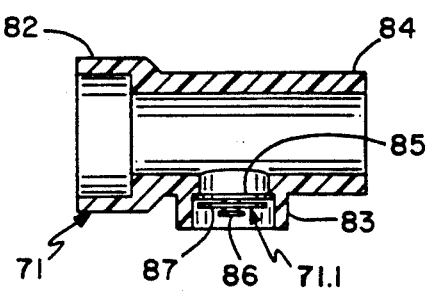
FIG. 7

DRUG DELIVERY DEVICE

The present invention relates to drug delivery devices for the delivery of aerosolized drugs to the lungs.

BACKGROUND OF THE INVENTION

Respiratory therapy may require the delivery of drugs directly to the lungs. The drugs conventionally prescribed are bronchodilators and inhalable steroids. Bronchodilators dilate the airways of the lungs by causing the smooth muscles of the airways to relax. Steroids reduce the swelling of inflammatory, allergic tissues of the airways. Some of the drugs typically prescribed are Alupent, Brethaire, Proventil, Ventolin and Albuterol.

Such respiratory drugs are typically delivered to the lungs via medication nebulizers which convert a liquid medication into a mist form. Nebulizers are conventionally connected in the inspiratory line running from a mechanical ventilator.

Respiratory drugs are also delivered in aerosol form from metered dose inhalers. Aerosol medication may be sprayed directly into the mouth, into a hand held spacer such as the AEROCHAMBER ® available from the Monaghan Medical Corporation, or directly into an inspiratory line with or without the aid of a spacer. One in-line spacer for connection into an inspiratory line is the AeroVent holding chamber available from the Monaghan Medical Corporation. The AeroVent holding chamber includes an accordian-like cylindrical wall which is expandable when an aerosol medication is delivered and which is collapsable after the medication has been dispensed. After it is collapsed, the AeroVent holding chamber remains connected in the inspiratory line and an internal conduit delivers fluid through the chamber. When medication is to be dispensed, the chamber folds out lengthwise and the conduit separates into two portions to create a spacer or holding chamber.

Whether aerosol medication or liquid medication by a nebulizer is being delivered to the lungs, particle size of the aerosolized medication is important. The greater the particle size, the greater the chance of loss of the medication by impaction on the inner walls of the spacer, inspiratory line, and upper airways where medication is ineffective. The smaller the particle size, the greater the potential that the medication will be carried to the more peripheral airways where the medication is effective.

One of the problems with a spacer having a cylindrical accordian-like wall is that it may expand or contract radially and axially. The resulting change in pressure and volume in the inspiratory line may cause a disruption in the operation of the mechanical ventilator which is set to respond to inspiratory efforts by a patient.

Another problem is that biocontaminated water may stand in the holding chamber when collapsed and provide an environment conducive to the growth of bacteria. When collapsed, fluid flows not through the holding chamber itself, but through an internal conduit. With moist air flowing through the internal conduit, moisture may migrate into the holding chamber upon expansion to contribute to the growth of bacteria.

Still another problem is that a cylindrical spacer is not directly connectable to a parallel wye connection without kinking the parallel wye connection or expiratory tube. Extensions may be inserted between the parallel wye connection and the cylindrical spacer, but extensions are undesirable because the spacer is thus disposed further from the lungs, thereby adding another piece of equipment and increasing the chances for impaction on the inner surfaces of the additional equipment.

SUMMARY OF THE INVENTION

A feature of the present invention is the provision in a spacer for delivery of an aerosolized therapeutic agent to the lungs by fluid being mixed with the agent and conveyed from an inlet to an outlet of the spacer, of means disposed adjacent the outlet for directing a therapeutic agent into the spacer toward the inlet of the spacer in retrograde fashion to facilitate a mixing of the therapeutic agent and fluid and the creation of an intact bolus before the therapeutic agent and fluid mixture are conveyed out of the spacer and into the lungs.

Another feature is the provision in such a spacer for delivery of an aerosolized therapeutic agent to the lungs and for connection in the inspiratory line running from a mechanical ventilator, of a frustoconical portion in the spacer to reflect the cone-like pattern formed by the spray from an aerosol canister and thereby minimize impaction of the therapeutic agent on the spacer.

Another feature is the provision in such a spacer for delivery of an aerosolized therapeutic agent to the lungs, of a baffle disposed between the inlet and outlet to deflect fluid in a direction oblique to the flow of fluid through the inlet and against the inner walls of the spacer where the therapeutic agent may impact or collect.

Another feature is the provision in a spacer for delivery of a therapeutic agent to the lungs and for connection in the inspiratory line running from a mechanical ventilator, of the spacer having rigid outer walls to maintain the desired pressure and volume of the fluid in the inspiratory line such that the mechanical ventilator may remain sensitive to the desired pressure, volume, or breathing of the patient.

An advantage of the present invention is that a greater quantity of a given dose of medication is delivered to the lungs instead of being lost by impaction on the inner surfaces of the spacer, inspiratory line, expiratory line or upper airways. With impaction, the amount of drug actually reaching the lower airways is unpredictable. When impaction is minimized, the amount of drug conveyed to the peripheral airways is increased. In particular, control over the actual amount of steroidal medication supplied to the lungs is important. Some of the features that contribute toward providing such an advantage are the frustoconical shape which rellects the cone-like spray pattern of the aerosol medication and hence reduces impaction, the baffle which directs air along the inner surfaces of the spacer to minimize impaction, and the direction of spray of the therapeutic agent which facilitates the creation of an intact bolus.

Another advantage is that a greater number of smaller particles of the therapeutic agent are delivered to the lungs. Aerosol medication includes a powdered drug and a liquid carrier. When sprayed, the liquid carrier evaporates to form a drug particle which is subsequently delivered to the lungs. Evaporation of the liquid carrier is enhanced by the baffle of the present spacer which facilitates a mixing of outside fluid and the aerosolized medication and a creation of a greater number of smaller particles.

Another advantage is that an intact bolus is delivered to the lungs. When aerosolized medication is sprayed downstream toward the lungs, a substantial amount of the medication dissipates downstream and disperses unrecoverably into the expiratory limb of the ventilator circuit before the inspiratory cycle is initiated. By directing the aerosolized medication in a retrograde fashion, such a loss is minimized if not eliminated. Moreover, since the baffle and its apertures direct fluid against the cone-like bolus from numerous directions, the bolus is carried as an intact whole into the lungs instead of being split apart by a single fluid stream.

Another advantage is that the therapeutic agent is delivered to the lungs in a more controlled fashion. With a rigid spacer, the volume and pressure of the inspiratory line is maintained, thus allowing a mechanical ventilator to remain sensitive to the breathing of the patient, as the volume and pressure of the inspiratory line are maintained at controllable levels. In contrast, spacers with flexible, accordian-like walls may tend to expand and contract with the changes in volume and pressure. Such spacers may dampen the normal responses of the ventilator to the patient's inspiratory effort, resulting in serious under-ventilation.

Another advantage is that a greater variety of patients may be administered aerosol medication. First, the ventilated, intubated patient may inhale aerosol medication via the spacer placed in-line with the inspiratory tube. Second, the nonventilated and spontaneously breathing patient who requires intubation may be assisted with administration of the aerosol medication with the spacer. Third, the nonintubated, spontaneously breathing patient may self-administer aerosol medication with the spacer.

Another advantage is that the spacer connects directly to a parallel wye connection. The tapering of the frustoconical spacer permits such a connection to the inspiratory tubular section of the parallel wye connection without a spreading of the parallel wye connection or a sharp bend or a kinking of the expiratory line which is connected to a parallel port of the parallel wye connection. The inspiratory and expiratory ports of such a parallel wye connection are disposed directly opposite and adjacent to each other in parallel fashion. Typically only inspiratory and expiratory lines are connected to the ports, as the diameters of the inspiratory and expiratory lines and parallel ports are the same.

Another advantage is that the frustoconical shape allows expansion of the sprayed therapeutic agent into a bolus while eliminating stagnant areas or corners which otherwise may harbor drug particles.

Another advantage is that the bolus thus formed by the sprayed therapeutic agent is delivered more quickly into the lungs. The tapering of the frustoconical portion toward the outlet acts like a funnel to enhance a washing out of the spacer as the mechanical ventilator delivers fluid from the inlet to the outlet. Respiratory therapeutic agents are more effective if delivered in the first one-third to one-half of the inspiratory cycle of the ventilator breath.

Another advantage of the present invention is that the spacer is inexpensive to manufacture and simple to install and operate.

Another advantage is that the present invention fits into all ventilator circuits: heated wire, non-heated, parallel wye, and conventional wye circuits.

BRIEF DESCRIPTION OF THE DRAWINGS

FIG. 1 is a perspective view of a mechanical ventilator with inspiratory and expiratory lines.

FIG. 2 is an elevation view of the present drug delivery device connected in the inspiratory line running from a mechanical ventilator such as shown in FIG. 1, and in a parallel wye connection cooperating with an endotracheal tube.

FIG. 3 is a detail elevational view of the drug delivery device of FIG. 2 with an aerosol canister containing a therapeutic agent shown in phantom.

FIG. 4 is a section view at lines 4—4 of FIG. 3.

FIG. 5 is a section view at lines 5—5 of FIG. 3.

FIG. 5A is an enlarged view of the therapeutic agent directing means of FIG. 4.

FIG. 6 is a section view of a one-way inlet valve connectable to the inlet of the drug delivery device of FIG. 4.

FIG. 7 is a section view of a one-way exhaust valve connectable to the outlet of the drug delivery device of FIG. 4.

FIG. 8 is a section view of an alternate embodiment of the drug delivery device.

FIG. 9 is a section view of an alternate embodiment of the drug delivery device.

FIG. 10 is a section view of an alternate embodiment of the drug delivery device.

FIG. 11 is a section view of an alternate embodiment of a drug delivery device connected downstream from a nebulizer.

DETAILED DESCRIPTION OF THE PREFERRED EMBODIMENT

As shown in FIGS. 2-5, the present drug delivery device is indicated in general by the reference numeral 10. It includes as its principal components a one-piece generally integral, rigid, transparent body or spacer 11 with an inlet 12 and outlet 13, a therapeutic agent directing means 14, and a baffle 15. An aerosol canister or metered dose inhaler 16 containing a therapeutic agent such as a bronchodilator or steroid includes a nozzle 17 which is insertable into the directing means 14.

As shown in FIGS. 1-2, the drug delivery device 10 is connectable to a mechanical ventilator 20. The mechanical ventilator 20 includes an inspiratory line 21 for conveying fluid, which is typically a mixture of oxygen and air, to an intubated patient 22. An expiratory line 23 conveys such a fluid, along with any fluids generated by the patient 22 or the therapeutic agent, back to the mechanical ventilator 20. A humidifier 24 is typically connected to the inspiratory line 21. A water trap or condensate collector 25 and spirometer 26 to measure exhaled volume are typically connected to the expiratory line 23. The ventilator 20 further includes a check valve to prevent backflow, and the expiratory line 23 further includes an exhalation valve which is closed during inspiration and controlled by air pressure.

The mechanical ventilator 20 is a positive pressure ventilator that forces fluid into the lungs 30 of the patient 22. In contrast, in the 1940's and 1950's, most ventilators used negative pressure (vacuum) to inflate the lungs. The body, except for the head, was enclosed in a gas tight chamber and a seal was placed around the neck. A motor driven bellows caused large pressure changes in the chamber, in turn causing pressure changes against the body. Since the patient's airway was outside the chamber, air moved in and out of the lungs. This was the iron lung. Some are still used. A modified version which encloses only the chest is called the Cuirass ventilator.

The vast majority of today's machines are positive pressure ventilators. In other words, the gas mixture is driven into the chest under positive pressure, through some sort of artificial airway such as a tracheostomy tube, which is inserted through an incision in the neck, or an endotracheal tube 32 passed through either the nose or the mouth and into the trachea. An inflatable cuff 33 at the end of the tube 32 seals against the trachea to prevent gas under pressure from escaping around the tube and back up the airway. The inspiratory phase of the ventilator 20 may be delivered in several different ways:

(i) a desired volume of gas is set on a dial or touch pad. An upper pressure limit is also set. If the pressure is reached before the set volume is delivered, gas flow stops. The ventilator then resets itself for the next breath and sounds an alarm that signals that the pressure limit was reached. This is referred to as "volume cycle, pressure limited" ventilation;

(ii) a desired pressure may be set as the primary cycling mechanism. This leaves the volume variable to changes in position, lung compliance, etc. This is referred to as pressure cycling; and (iii) the third method of delivering the inspiratory phase is referred to as timed cycling and is related to the flow rate of the gas being delivered during inspiration. The shorter the time, the greater the flow, and vice versa, if the volume is constant.

Inspiration can be initiated in one of two ways:

(i) a timing device in the ventilator causes each breath to be delivered. For example, for a rate of 12 breaths per minute, the machine would delivery a breath every five seconds. A rate of 10 breaths per minute would result in a breath every six seconds; or (ii) the ventilator can be set to be sensitive to the patient's own inspiratory efforts (if present). In this system, whenever the patient attempts to take a breath on his own, the machine responds by delivering a breath of the set volume. Usually a minimum number of breaths per minute is set, so if a patient's respiratory rate falls below that value or stops all together, the machine will assume a pattern according to that value. This is referred to as "assist/control" and is the most common form of ventilation.

Most positive pressure ventilators allow exhalation to occur passively. A valve, either in the tubing circuit or in the machine, opens when inspiration stops. This causes a release of the pressure built up during inspiration, and gas flows out of the lungs.

The spacer 11 includes a rigid frustoconical spacing portion 40 which tapers toward the outlet 13 and which includes larger and smaller diametrical ends 40.1 and 40.2. The frustoconical portion 40 includes an inner surface 41 and interior 42. Substantially all of the diametrical sectional slices of the spacing portion 40 have diameters greater than the diameter of the outlet 13 and inspiratory line 21 to allow expansion of the drug bolus. One reason for the frustoconical feature of portion 40 is to simulate or reflect the conical spray pattern of the aerosol therapeutic agent. Another reason for the frustoconical shape of portion 40 is to facilitate connection to the inspiratory port of the parallel wye connection 43. Still another reason for the frustoconical shape is to enhance washout of the therapeutic agent and eliminate stagnant areas that otherwise may trap moisture or particles of the therapeutic agent.

The frustoconical portion 40 is integrally connected via an annular rib 45 to a tapering portion 46 which tapers toward and is integrally connected to the inlet 12. The tapering portion 46 encompasses the baffle 15 which directs fluid in a direction oblique of the direction of fluid flowing through the inlet 12 and toward the inner surface 41 of the frustoconical portion 40. The baffle 15 includes an inner cone-like portion or first deflector 47 running substantially parallel to the tapering portion 46 to form an oblique passage 47.1. The first deflector 47 is frustoconical in shape and tapers toward and is integrally connected to an apertured disc or second deflector 48 with a set of three apertures 49 which permit fluid flow into the interior 42 directly from the inlet 12. A greater or lesser number of apertures of larger or smaller size may be formed in the disc 48.

An undulating band or third deflector 50 secures the disc 48 and inner cone-like portion 47 to the tapering portion 46. The undulating band 50 includes respective proximal and distal semicircular recesses 51, 52 alternating about its circumference to allow fluid flow into the oblique passage 47.1 and into the interior 42. It should be noted that the drug delivery device 10 may be used without the baffle 15, but use of the baffle 15 is typically preferable.

The inlet 12 is tubular and typically is inserted inside the inspiratory line 21. The outlet 13 is also tubular and typically is inserted over the inspiratory port of the parallel wye connection 43. It should be noted that the drug delivery device 10 is connectable to all types of wye connections such as bifurcated wyes, F-wyes and swivel wyes.

The therapeutic agent directing means 14 is fixed in and to the outlet 13. The directing means 14 includes a cylindrical retainer 55 affixed to the outer surface of the outlet 13 to stably receive the aerosol canister 16 and to provide an abutment means which prevents a tipping of the aerosol canister 16 when the therapeutic agent is sprayed. A rod-like stem 56 is secured to the cylindrical wall of the outlet 13 and extends into the outlet 13. The stem 56 is disposed axially relative to the cylindrical retainer 55 and includes a passage 57. At its upper end, the passage 57 includes a nozzle receiving portion 58 for receiving the nozzle 17 of the aerosol canister 16. The nozzle receiving portion 58 is formed in part by an annular shoulder or stop 59 for bearing against the end 60 of the nozzle 17. At the annular shoulder 59, the passage portion 58 communicates with a passage portion 61. Both passage portions 58, 61 are formed axially in the rod-like stem 56. Passage portion 61 communicates with an outlet passage portion 62. Passage portion 62 shares a common axis with inlet 12, outlet 13 and frustoconical portion 40 such that the therapeutic agent is sprayed uniformly into the conical portion 40. As the end 60 of the nozzle 17 bears on the annular shoulder 59 and pressure is brought to bear on the aerosol canister 16 such that the canister 16 is pushed closer to the cylindrical wall of the outlet 13, the nozzle 17 is forced into the aerosol canister 16 to trigger the release of the therapeutic agent. An aerosolized therapeutic agent is thereby sprayed through passage portions 61, 62 and in a conical pattern into the interior 42 of the frustoconical portion 40.

In operation, when the patient 22 requires a therapeutic agent such a bronchodilator or steroid, the inspiratory line 21 is disconnected from the parallel wye connection 43. The inlet 12 of the device 10 is then connected substantially horizontally in the inspiratory line 21 and the outlet 13 of the device 10 is slipped over the inspiratory port of the parallel wye connection 43. The aerosol canister 16 and its nozzle 17 are then inserted in the cylindrical retainer 55 and nozzle receiving portion 58, respectfully. Immediately before the inspiratory phase or fluid as designated by the letter A is delivered by the mechanical ventilator 20, the therapeutic agent is sprayed into the spacer 11, as designated by the letter B. After the therapeutic agent has formed a cone-like pattern or bolus in the spacer 11, air or oxygen conveyed by the ventilator 20 enters the inlet 12 and subsequently passes into the interior 42 of the spacer 11 via the apertures 49 and oblique passage 47.1. The fluid thus conveyed mixes with the aerosolized medication to evaporate the liquid carrier and create particles of medication. The fluid thus conveyed also impinges on the bolus from numerous directions to direct the bolus as an intact whole into the lungs. Moreover, such fluid flowing through the passage 47.1 and apertures 49 creates some turbulence in the interior 42. Such turbulence also contributes to a greater mixing. Accordingly, a lesser amount of therapeutic agent is lost to impaction, particle size may be reduced, and a greater amount of agent is delivered out of the outlet 13 and into the lungs 30. After the desired amount of therapeutic agent is delivered, the drug delivery device 10 is disconnected from the inspiratory line 21 which is reconnected to the parallel wye connection 43.

One of the reasons for the disconnection of the drug delivery device 10 from the inspiratory line 21 is to maintain a relatively bacteria free environment. Fluid delivered by the mechanical ventilator 20 is typically warmed and moistened by the humidifier 24 and such moisture tends to cling to surfaces and collect in the inspiratory line 21 and other devices connected in line with the inspiratory line 21. These moist warm areas may nurture the growth of bacteria. Since the present invention is designed to be removed between uses and allowed to dry, the danger of biocontamination is reduced if not eliminated.

As shown in FIGS. 6 and 7, an alternate embodiment of the invention includes valved tubular extensions 70, 71 for being connected to the inlet 12 and outlet 13, respectively. When the extensions 70, 71 are connected as such, the drug delivery device 10 is in its preferred form for the delivery of bronchodilators or steroids to the intubated, spontaneously breathing patient who may self-administer or be assisted with administration of the therapeutic agent or to the nonintubated, spontaneously breathing patient who typically self-administers the drug. However, the drug delivery device 10 may be used by the nonintubated, spontaneously breathing patient without the valved extensions 70, 71 and wherein the outlet 13 serves as a mouthpiece.

As shown in FIG. 6, extension 70 includes an inlet 72 and an outlet 73. Outlet 73 slides over the inlet 12 of the drug delivery device 10. A one-way inlet valve 70.1 includes an apertured disc 74 with an axial post 75 secured in the extension 70 between the inlet 72 and the outlet 73. A flexible disc 76 distorts on the post 75 and is drawn away from the apertured disc 74 when fluid is drawn from the inlet 72 to the outlet 73 to thereby allow fluid flow through the apertured disc 74. The flexible disc 76 is pushed against the aperture disc 74 when fluid flows from the outlet 73 to the inlet 72, such as when a patient exhales to prevent fluid flow through the aperture disc 74 and valve 70.1.

As shown in FIG. 7, extension 71 includes an inlet 82, an outlet 83 and a mouthpiece 84. The outlet 83 includes a one-way exhaust valve 71.1 comprising an apertured disc 85 and a post 86. The apertured disc 85 is secured in the outlet 83. A flexible disc 87 rides on the post 86 and is drawn against the aperture disc 85 when fluid flows from the inlet 82 to the mouthpiece 84 such as when a patient inhales, to thereby prevent fluid flow through the outlet 83. When a patient exhales and fluid pressure builds in the drug delivery device 10 and between the inlet 82 and mouthpiece 84, the flexible disc 87 is pushed away from the aperture disc 85 and fluid flows from the valve 71.1 through the outlet 83.

In operation, the patient slips the extensions 70, 71 over the respective inlet 12 and outlet 13 of the drug delivery device 10. The aerosol canister 16 and nozzle 17 are then inserted into the cylindrical retainer 55 and nozzle receiving portion 58. The patient places his or her mouth over the mouthpiece 84 and exhales such that fluid flows through the outlet 83. Immediately before inhaling, the therapeutic agent in the aerosol canister 16 is sprayed into the spacer 11. As the patient then inhales, air is drawn through the valve 70.1 and is drawn into the interior 42 of the spacer 11 via the apertures 49 and oblique flow passage 47.1. As the therapeutic agent fans out into a cone-like pattern, air drawn through the oblique flow passage 47.1 minimizes impaction on the inner surface 41. Mixing is enhanced and some turbulence is created as air flowing through the apertures 49 and oblique passage 47.1 flows against the spray direction of the therapeutic agent. As well as contributing to a greater mixing of air and therapeutic agent, these factors contribute to reduction of particle size of the therapeutic agent. As the patient continues to inhale, the therapeutic agent and air mixture is drawn through the mouthpiece 84 and into the lungs. The patient may then remove the drug delivery device 10 and mouthpiece 84 from his or her mouth to exhale, or exhale into the mouthpiece 84 to exhaust air through the outlet 83 and valve 71.1.

As shown in FIGS. 8–10, alternate embodiments of the invention include cylindrical spacers 90, 91, 92. Spacer 90 includes rounded ends 95 adjacent to an inlet 96 and an outlet 97. Spacer 90 also includes an apertured baffle similar to baffle 15 with the exception that the baffle in spacer 90 includes a rounded deflector wall 99 instead of a frustoconical wall portion 47. Spacer 90 further includes a cylindrical retainer 100 set in the spacer 90 for the aerosol canister 16 as shown in FIGS. 4 and 8, it should be noted that the height of each of the retainers 55, 100 is at least as great as the width of each of the respective retainers 55, 100.

As shown in FIG. 9, spacer 91 includes an inlet 105 and an outlet 106. The outlet 106 houses the therapeutic agent directing means 14. As shown in FIG. 10, spacer 92 includes an inlet 110, an outlet 111 with the inlet 110 housing the therapeutic agent directing means 14. In this embodiment, therapeutic agent is sprayed in the direction of fluid flow, although such a spray direction is less preferred.

As shown in FIG. 11, the spacer 11 may be utilized with a nebulizer 115. In such a use, one port of a T-fitting 116 is slipped onto the inlet 12 of the spacer 11 and the one way exhaust valved extension 71 is slipped onto the outlet 13. The one way inlet valved extension 70 is slipped onto the other linear port of the T-fitting 116 and the nebulizer 115 is inserted into the remaining port of the T-fitting 116. The nebulizer 115 includes liquid medication 117 which is drawn through a tube 118 by oxygen or air being passed by and creating a low pressure over the outlet of the tube 118. The oxygen or air is conveyed by tube 119 running from a compressed gas source and connecting to the exterior of the nebulizer 115. From tube 119, the oxygen or air flows into internal tube 120 which has an outlet adjacent the outlet tube 118. Fluid flowing from the internal tube 120 creates the low pressure over the outlet of outlet tube 118 and atomizes the liquid mediation drawn up through the tube 118 to an aerosolized form.

In operation, a nonintubated patient exhales and then places his or her mouth on the mouthpiece 84 to inhale medication generated by the nebulizer 115. During inhalation, air is drawn in through the one-way inlet valve 70.1 and the aerosolized medication created by the atomizing tubes 118, 120 is drawn from the spacer 11 via the T-fitting 116. As the air and medication is drawn into the spacer 11, the medication and air are mixed by the baffle 15 before being inhaled into the lungs. Such mixing dries the aerosolized medication and thereby reduces particle size of the medication for a more effective therapeutic treatment. An intubated patient may have the device attached to the endotracheal or tracheostomy tube.

It should be noted that the spacer 11 may be opaque or translucent.

The present invention may be embodied in other specific forms without departing from the spirit or essential attributes thereof; therefore, the illustrated embodiment should be considered in all respects as illustrative and not restrictive, reference being made to the appended claims rather than to the foregoing description to indicate the scope of the invention.

What is claimed:

1. A drug delivery device for connection in a mechanical ventilator circuit having inspiratory and expiratory lines and being controlled by a mechanical ventilator, the circuit including a wye connection for connecting the inspiratory and expiratory lines, the device being connected to the inspiratory line between the mechanical ventilator and a patient for administering an aerosolized therapeutic agent to the patient, the mechanical ventilator conveying fluid from the ventilator, through the inspiratory line and drug delivery device, and to the patient, the drug delivery device comprising:
   a spacer with an inlet and an outlet and being connected in the inspiratory line such that fluid flows from the inlet to the outlet, the spacer having a spacing portion with a width greater than the width of the outlet;
   directing means for directing the therapeutic agent into the spacer, the directing means disposed adjacent to the spacing portion; and
   means for minimizing loss of the therapeutic agent to the expiratory line, the means for minimizing loss including the spacer being connected adjacent to the wye connection and between the wye connection and the mechanical ventilator, the means for minimizing loss further including the directing means being structured to direct the therapeutic agent in a direction opposite the fluid flow and away from the wye connection such that loss of the therapeutic agent to the expiratory line is minimized and to facilitate a mixing of the therapeutic agent and fluid before the therapeutic agent and fluid are conveyed out of the outlet and into the lungs, the therapeutic agent being fluidly redirected after such mixing by the fluid flow from the inlet to the outlet.

2. The device according to claim 1, wherein the spacing portion includes a tapering portion with larger and smaller diametrical ends, the smaller diametrical end disposed adjacent to the outlet.

3. The device according to claim 1, wherein the spacer includes a baffle between the inlet and outlet to deflect at least a portion of the fluid in a direction oblique to fluid flow through the inlet.

4. The device according to claim 3 and the spacing portion including an inner surface, wherein the baffle includes a deflector adjacent the inlet and positioned obliquely to the fluid flow through the inlet such that the deflector directs at least a portion of the fluid to the inner surface of the spacing portion.

5. The device according to claim 3 and the spacing portion including an interior, wherein the baffle includes an aperture for allowing fluid to flow through the baffle and into the interior of the spacing portion.

6. The device according to claim 1., wherein the spacer includes a cylindrical portion with a diameter greater than the width of the outlet.

7. The device according to claim 1 and the spacer including an exterior and an interior, wherein the directing means comprises a stem including an inlet portion, an outlet portion, and a passage running from the inlet portion to the outlet portion, the inlet portion being accessible from the exterior of the spacer, the outlet portion being in the interior of the spacer and structured to direct the therapeutic agent toward the inlet of the spacer.

8. The device according to claim 7, and further comprising an aerosol canister with a nozzle, the aerosol canister housing an aerosolizable medication which includes the therapeutic agent, the nozzle being insertable in the inlet portion to spray the therapeutic agent into the spacer.

9. The device according to claim 8, wherein the directing means includes a retainer surrounding the inlet portion of the stem such that aerosol canister is stably receivable in the retainer and the nozzle is stably insertable in the inlet portion when the medication is aerosolized.

10. The device according to claim 9, wherein the height of the retainer is at least as great as the width of the retainer.

11. The device according to claim 2, wherein the tapering portion comprises a frustoconical portion.

12. The drug delivery device according to claim 1, wherein the spacer is disposed substantially horizontally when connected in the inspiratory line.

13. A drug delivery device for connection in a mechanical ventilator circuit having inspiratory and expiratory lines and being controlled by a mechanical ventilator, the device being connected to the inspiratory line between the mechanical ventilator and a patient for administering an aerosolized therapeutic agent to the patient, the mechanical ventilator conveying fluid from the ventilator, through the inspiratory line and drug delivery device, and to the patient, the drug delivery device comprising:
   a spacer with an inlet and an outlet and being connected in the inspiratory line such that fluid flows from the inlet to the outlet, the inlet and outlet being coaxial, the spacer having a spacing portion with a width greater than the width of the outlet;
   directing means on the spacer for directing the therapeutic agent into the spacer; and
   a baffle between the inlet and outlet to deflect at least a portion of the fluid in a direction oblique to the fluid flow through the inlet, the baffle being coaxial with the inlet and outlet, the baffle including a deflector adjacent the inlet and positioned obliquely to the fluid flow through the inlet such that the deflector directs at least a portion of the fluid to flow along the inner surface of the spacer, the baffle further including apertures to permit at least a portion of the fluid to flow through the baffle, the directing means disposed to direct the therapeutic agent between the outlet and the baffle whereby the fluid engages the baffle before mixing substantially with the therapeutic agent.

14. A hand-held drug delivery device for mixing an aerosolized therapeutic agent with ambient air and for effective delivery of the aerosolized therapeutic agent to the lungs of a spontaneously breathing patient, the aerosolized therapeutic agent originating from a cylindrical aerosol canister, the drug delivery device comprising:

a spacer with an inlet and an outlet and the ambient air being drawn into the inlet and from the inlet to the outlet by the patient, the spacer having a spacing portion with a width greater than the width of the outlet;

directing means on the spacer for directing the therapeutic agent into the spacer and structured to direct the therapeutic agent in a direction from the outlet to the inlet;

a one-way inlet valve connectable to the inlet to allow fluid into the spacer and prevent fluid flow from the spacer via the inlet vale;

a T-piece connectable adjacent the outlet and comprising a one-way outlet valve to allow fluid flow out of the spacer and prevent fluid flow into the spacer via the outlet valve, the T-piece comprising three ports, one of the ports housing the outlet valve, another port being a mouthpiece, and still another port being connectable adjacent the outlet; and a cylindrical retainer adjacent the directing means for engaging the cylindrical aerosol canister, the height of the retainer being at least as great as the diameter of the retainer to stably receive the cylindrical aerosol canister.

15. A drug delivery device for connection in a mechanical ventilator circuit having inspiratory and expiratory lines and being controlled by a mechanical ventilator, the device connected to the inspiratory line between the mechanical ventilator and a patient for administering an aerosolized therapeutic agent to the patient from a cylindrical aerosol canister with a nozzle, the mechanical ventilator conveying fluid from the ventilator, through the inspiratory line and drug delivery device, and to the patient, the drug delivery device comprising:

a spacer with an inlet and outlet connected in the inspiratory line such that fluid is conveyed from the inlet to the outlet, the inlet and outlet being cylindrical and coaxial with each other, the spacer having a spacing portion with a maximum width greater than the width of the outlet, the spacing portion having a length;

directing means for directing the therapeutic agent into the spacer, the directing means disposed adjacent to the spacing portion and structured to direct the therapeutic agent in a direction from the outlet to the inlet and coaxial with the inlet and outlet to facilitate a mixing of the therapeutic agent and fluid before the therapeutic agent and fluid are conveyed out of the outlet and into the lungs, the directing means further comprising a cylindrical retainer on the outlet to support the aerosol canister when its nozzle is in the inlet portion;

the spacing portion comprising a rigid frustoconical inner surface portion which extends outwardly from the outlet to the maximum width of the spacing portion, the spacing portion tapering from the maximum width to the inlet whereby the frustoconical portion reflects a cone-like spray pattern of the aerosolized therapeutic agent.

16. A hand-held drug delivery device for mixing an aerosolized therapeutic agent with ambient air for effective delivery of the aerosolized therapeutic agent to the lungs of a spontaneously breathing patient, the aerosolized therapeutic agent originating from a cylindrical aerosol canister having a nozzle, the drug delivery device comprising:

a spacer with an inlet and outlet and the ambient air being drawn into the inlet and from the inlet to the outlet by the patient, the inlet and outlet being cylindrical and coaxial with each other, the spacer having a spacing portion with a maximum width greater than the width of the outlet, the spacing portion extending to and between the inlet and outlet and being coaxial with the inlet and outlet, the spacing portion also having a length;

directing means for directing the therapeutic agent into the spacing portion, the directing means mounted on the outlet and structured to direct the therapeutic agent in a direction from the outlet to the inlet and said directing means being coaxial with the inlet and outlet to facilitate a mixing of the therapeutic agent and ambient air before the therapeutic agent and ambient air are drawn out of the outlet and into the lungs, the directing means further including a stem, the stem including an inlet portion, an outlet portion and a passage running from the inlet portion to the outlet portion, the outlet portion being in the outlet, the outlet portion being coaxial with the inlet and outlet, the directing means further comprising a cylindrical retainer surrounding the inlet portion to support the aerosol canister when its nozzle is in the inlet portion;

the spacing portion comprising a frustoconical and rigid portion which extends outwardly from the outlet to the maximum width of the spacing portion, the spacing portion tapering from the maximum width to the inlet whereby the tapering portion reflects the aerosolized therapeutic agent which forms a tapering pattern when aerosolized; and valve means on the spacer for regulating inhalation and exhalation relative to the spacer.

17. A drug delivery device for connection in a mechanical ventilator circuit having inspiratory and expiratory lines and being controlled by a mechanical ventilator, the device being connected to the inspiratory line between the mechanical ventilator and a patient for administering an aerosolized therapeutic agent to the patient, the mechanical ventilator conveying fluid from the ventilator, through the inspiratory line and drug delivery device, and to the patient, the drug delivery device comprising:

a spacer with an inlet and an outlet and being connected in the inspiratory line such that fluid flows from the inlet to the outlet, the spacer having a spacing portion with a width greater than the width of the outlet;

directing means for directing the therapeutic agent into the spacer, the directing means disposed adjacent to the spacing portion; and means for minimizing loss of the therapeutic agent to the expiratory line including the directing means being structured to direct the therapeutic agent in a direction opposite the fluid flow such that loss of the therapeutic agent to the expiratory line is minimized and to facilitate a mixing of the therapeutic agent and fluid before the therapeutic agent and fluid are conveyed out of the outlet and into the lungs, the therapeutic agent being fluidly redirected after such mixing by the fluid flow from the inlet to the outlet.

* * * * *